United States Patent [19]

Wilke et al.

[11] 3,972,775

[45] Aug. 3, 1976

[54] CONVERSION OF CELLULOSIC MATERIALS TO SUGAR

[75] Inventors: Charles R. Wilke, El Cerrito; Gautam Mitra, Berkeley, both of Calif.

[73] Assignee: The United States of America as represented by the United States Energy Research and Development Administration, Washington, D.C.

[22] Filed: June 28, 1974

[21] Appl. No.: 484,010

[52] U.S. Cl. .............................. 195/33; 195/100; 195/115
[51] Int. Cl.² ................. C12D 13/02; C12B 3/08
[58] Field of Search ............... 195/33, 115, 99, 11, 195/7, 104, 4, 8, 9, 10, 66 R, 63, 68, 100

[56] References Cited
UNITED STATES PATENTS

| | | | |
|---|---|---|---|
| 3,462,275 | 8/1969 | Bellamy | 195/104 |
| 3,616,222 | 10/1971 | Dasinger | 195/33 |
| 3,642,580 | 2/1972 | Ghose | 195/33 |
| 3,711,392 | 1/1973 | Metzger | 195/33 |
| 3,734,831 | 5/1973 | Hulme | 195/66 R |
| 3,764,475 | 10/1973 | Mandels et al. | 195/33 |
| 3,812,013 | 5/1974 | Bellamy et al. | 195/33 |

OTHER PUBLICATIONS

Mandels et al., "The Production of Cellulose," Cellulases and Their Applications, Gould Ed. A.C.S. Publications Washington, D.C. (1969) pp. 391-396.

*Primary Examiner*—A. Louis Monacell
*Assistant Examiner*—Thomas G. Wiseman
*Attorney, Agent, or Firm*—Dean E. Carlson; F. A. Robertson; Irene S. Croft

[57] ABSTRACT

A process for the production of sugar, mainly glucose, by the enzymatic degradation of cellulosic materials, particularly cellulosic wastes, which comprises hydrolyzing the cellulosic material in the presence of cellulase enzyme to produce a sugar solution and recovering from the hydrolysis products a major proportion of the cellulase enzyme used in the hydrolysis reaction for re-use. At least a portion of the required makeup cellulase enzyme is produced in a two-stage operation wherein, in the first stage, a portion of the output sugar solution is utilized to grow a cellulase-secreting microorganism, and, in the second stage, cellulase enzyme formation is induced in the microorganism-containing culture medium by the addition of an appropriate inducer, such as a cellulosic material. Cellulase enzyme is precipitated from the culture liquid by the addition of an organic solvent material, such as a low molecular weight alkyl ketone or alcohol, and the cellulase precipitate is then fed to the hydrolysis reaction.

9 Claims, 1 Drawing Figure

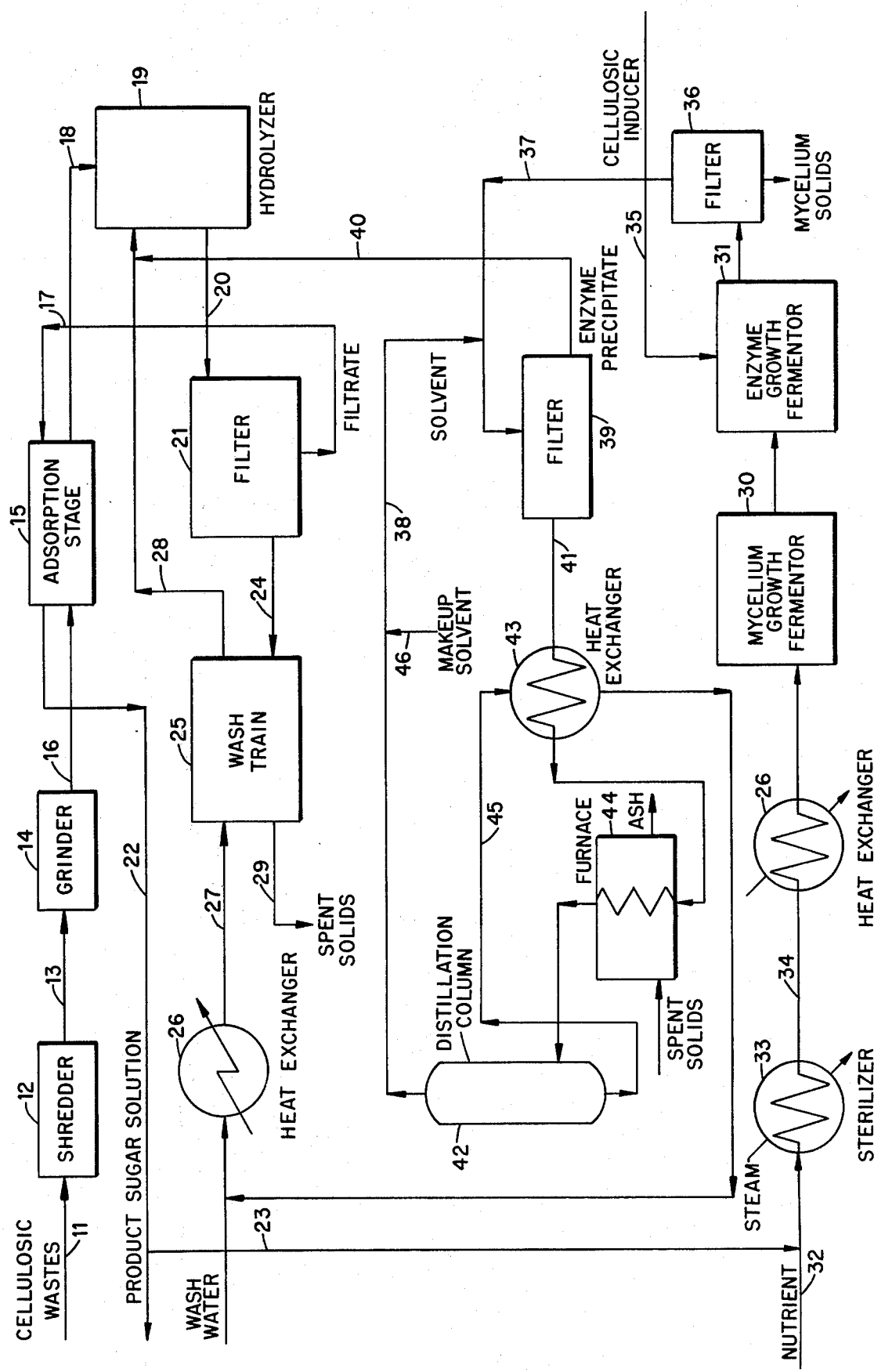

CONVERSION OF CELLULOSIC MATERIALS TO SUGAR

The invention disclosed herein was made in the course of, or under, Contract No. W-7405-ENG-48 with the United States Atomic Energy Commission.

BACKGROUND OF THE INVENTION

This invention relates to the enzymatic hydrolysis of cellulosic materials, particularly cellulosic wastes.

Hydrolysis of cellulose yields a mixture of simple reducing sugars, mainly glucose. These hydrolysis products can be converted to ethyl alcohol which can be used as a liquid fuel to replace petroleum, or they can be converted to methane which can be a useful source of gaseous fuel. Or the hydrolysis products can be used to manufacture various organic chemicals presently produced from petroleum. In terms of available energy, expressed either as the heat of combustion of cellulose or of the glucose or alcohol theoretically obtainable therefrom, a pound of cellulose is equivalent to 0.35 lb of gasoline (7200 BTU).

On the land area of the earth about $1.6 \times 10^{10}$ tons of carbon are fixed every year by photosynthesis, out of which about half appears in the form of cellulose. The sheer magnitude of this potential source dictates the necessity of improving the scientific and technological capabilities for cellulose utilization. In the North American continent certain cellulosic materials are available for economic processing at this time. Two hundred ninety million tons per year of residential, institutional and commercial solid wastes containing approximately fifty percent paper and other cellulosic materials are produced in the United States. In addition, about sixty million tons of bagasse are available. These altogether contain about one hundred and twenty million tons of cellulose, the energy equivalence of which is about a fifth of the current U.S. gasoline consumption. Furthermore, 2.3 billion tons per year of agricultural wastes in the United States, having a very high cellulose content, increase the supply significantly. In spite of these various sources of available cellulose, a major industrial alcohol fermentation process can only be successful if the reducing sugars are available at a sufficiently low price.

Most early efforts in this field were geared to the acid hydrolysis of wood products to sugars. The most notable process in this context was the Bergius process in the 1930's (Bergius, F., *Ind. Eng. Chem.*, 29, 247, 1937). However, acid hydrolysis requires costly materials of construction because of the inherent problems of corrosion. In recent years, cellulose degradation through enzymatic means has been a subject of investigation by various workers.

SUMMARY OF THE INVENTION

It is an object of this invention to provide an efficient and economical method for the utilization of cellulosic materials.

More specifically, it is an object of this invention to provide a process for the production of sugar by the enzymatic hydrolysis of cellulosic materials, particularly cellulosic wastes.

It is a further object of the invention to recover for recycling a major proportion of the enzyme used in the hydrolysis of cellulosic materials.

It is still a further object of the invention to produce the necessary makeup enzyme for the hydrolysis of the cellulosic materials by utilizing a portion of the output sugar solution.

In accordance with the present invention, there is provided a process for the conversion of cellulosic materials, particularly cellulosic wastes, to sugar which comprises hydrolyzing the cellulosic material in the presence of cellulase enzyme, thereby converting the cellulose to sugar, and recovering from the hydrolysis products cellulase enzyme for recycling to the hydrolysis reaction and a solution containing product sugar.

More specifically, in the present invention, the products of the enzymatic hydrolysis of the cellulosic material are separated into a liquid sugar-containing phase and a solid phase containing unhydrolyzed solids. Both of these phases contain cellulase enzyme from the hydrolysis stage. The solid phase is washed with water for recovery of enzyme adsorbed thereon, and the resulting wash water containing recovered enzyme is then fed to the hydrolysis reaction. The liquid sugar-containing phase is contacted with incoming cellulosic solids whereby the enzyme contained therein is adsorbed on the solid material which is then introduced into the hydrolysis vessel. A major proportion of the cellulase enzyme used in the hydrolysis reaction can thus be recovered from the hydrolysis products. The liquid sugar-containing stream from the adsorption step is the product stream of the process.

In a particular mode of operation of the invention, a portion of the product sugar stream is utilized to produce at least a portion of the required makeup enzyme by the steps comprising growing a cellulase-synthesizing microorganism thereon and inducing cellulase enzyme formation in the microorganism-containing culture medium by the addition of an appropriate inducer such as a cellulosic material. Since the amount of cellulase enzyme recovered by the above-described washing of unhydrolyzed solids is a function of the amount of wash water used, it is preferable to feed makeup enzyme in solid form to the hydrolysis reaction in order to maximize the amount of water utilized in the washing step. Precipitation of the makeup cellulase enzyme from the culture medium after the removal of solids therefrom is accomplished by organic solvent extraction. The precipitated enzyme is then introduced into the hydrolysis reaction to provide makeup enzyme.

The cellulose molecule is a high molecular weight polymer of $\beta$-1,4-linked D-glucose residues, the degree of polymerization varying widely depending upon its origin. For chemical pulp and filter paper the degree of polymerization generally varies between 500 and 1000, whereas in wood cellulose it is about 8000 – 10,000. During enzymatic hydrolysis by cellulase enzyme, $\beta$-1,4 glucosyl bonds are split to produce a mixture of simple reducing sugars, mainly glucose, according to the following equation:

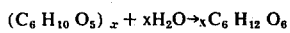

The terms "cellulase" and "cellulase enzyme" are used herein to designate a complex system of enzymes (molecular weight range 12,000 – 68,000) showing various types of activities with respect to different kinds of substrates. Although the degradation of crystalline cellulose by enzymatic means has been the object of intense study for the last 25 years, the exact mechanism thereof is not yet entirely clear. The most accepted postulate in this area has been the two step $C_1 - C_x$ theory proposed by Reese et al., *J. Bacteriol.*, 59, 485

(1950). According to this theory the $C_1$ component of the enzyme first disintegrates the cellulose chain prior to its solubilization. The subsequent hydrolytic action at the $\beta$-1,4 linked glucosyl bonds of the solubilized chain is attributed to the $C_x$ component of the enzyme. The results of various other workers in the field combine to postulate an alternative hypothesis according to which it is the $C_x$ component which delivers the initial attack on the cellulose chain by random action, producing fragments of lower molecular weight which can then be acted upon by the $C_1$ component by an endwise (exo) mechanism producing cellobiose residues.

Cellulase activities are measured by interacting a given substrate with the enzyme and measuring the amount of reducing sugar produced in a given time. One such test is the Filter Paper activity test which measures combined $C_1 - C_x$ activity. In this test, 50 mg (1 × 6 cm) of Whatman Filter Paper No. 1 is added to a mixture of 1 ml of appropriately diluted enzyme and 1 ml of 0.05 M sodium citrate buffer at pH of 4.8. Reaction is carried out at 50°C for 1 hour and reducing sugar concentration determined by dinitrosalicylic acid test. Filter Paper activity is expressed as milligrams of reducing sugar produced by the undiluted enzyme sample.

The cellulase enzyme used in the hydrolysis step of the present invention is synthesized by certain cellulolytic microorganisms which are capable of producing both $C_1$ and $C_x$ components. This group of microorganisms includes *Trichoderma viride*, *Trichoderma koningii*, *Fusarium solani*, *Penicillium funiculosum*, and the like. (See American Type Culture Collection, *Catalogue of Strains*, Ninth Edition, 1970.) Of these, the fungus *Trichoderma viride*, particularly *T. viride* QM9414 which is a mutant strain obtained by irradiating conidia of *T. viride* QM6a with a linear accelerator and which is obtainable from U.S. Army Natick Laboratories in Massachusetts, has been found to be especially productive in the synthesis of cellulase.

BRIEF DESCRIPTION OF THE DRAWING

The invention is illustrated in the accompanying drawing wherein the single FIGURE is a flow diagram of a particular mode of operation of the cellulose conversion process of the present invention.

DETAILED DESCRIPTION OF THE INVENTION

Referring now to the drawing in detail, waste cellulosic material, such as waste paper, is introduced by means of line 11 into shredder 12 and then discharged via line 13 into grinder 14 where it is ground to a suitable particle size if necessary. The ground waste is then fed to adsorption stage 15 by way of line 16 where it is contacted with filtrate solution from the hydrolyzer reaction. Filtrate solution is introduced into the adsorption stage by way of line 17. Adsorption stage 15 is preferably a train of countercurrent mixer-filters. The ground waste is then conveyed by way of line 18 to hydrolyzer 19 which consists preferably of a plurality of agitated cylindrical concrete digesters of the type generally used in solid waste treatment in sanitary engineering. In hydrolysis section 19, the ground waste is contacted with cellulase enzyme protein at a temperature from substantially 30°C to substantially 60°C, preferably around 50°C, for a period of time sufficient to effect conversion of a substantial proportion of the cellulose into sugar. Temperatures much above substantially 60°C will tend to denature the cellulase enzyme. The amount of time required for hydrolysis depends upon the concentration of the cellulase enzyme present. Generally, the concentration should be such as to provide an enzyme activity of from substantially 0.5 to substantially 6 Filter Paper units which corresponds to a concentration of from substantially 0.2 to substantially 5 mg/ml of enzyme protein. The upper limit of cellulase concentration is determined by the solubility of the enzyme protein in solution while the lower limit is dictated by economic considerations. It has been found that an enzyme activity of from substantially 2 to substantially 3 Filter Paper units is most efficacious. The solution in the hydrolysis section is maintained preferably on the acid side, that is, at a pH of from about 4 to about 6.

Following hydrolysis, the effluents are discharged by way of line 20 to filter 21 where a liquid sugar-containing phase is separated from a solids phase. The liquid sugar-containing stream from filter 21 enters adsorption stage 15 by means of line 17, as noted above, to recover cellulase enzyme in the liquid phase by adsorption on incoming cellulosic solids. The cellulosic solids with the recovered enzyme protein adsorbed on them are then fed to hydrolyzer 19 via line 18 as noted above. The liquid stream leaving adsorption section 15 via line 22 is the product stream of the process and consists of a mixture of simple reducing sugars, mainly glucose. A portion of the output stream, less than about 15% by weight, for example, of the order of from substantially 6% to substantially 10%, is removed by means of line 23 and utilized in the enzyme makeup section for the growth of fungal microorganism as hereinafter described.

The filtered unhydrolyzed solids leave filter 21 by way of line 24 and enter wash train 25, which is preferably a plural stage countercurrent mixer-filter, for the recovery of adsorbed enzyme by washing with process water at a temperature and pH corresponding to that in the hydrolysis section. The wash water, which can be heated to process temperature in heat exchanger 26 by the makeup enzyme stream, is introduced into wash train 25 by way of line 27. The liquid stream containing desorbed enzyme is then fed to hydrolyzer 19 by way of line 28, and the spent solids, which are discharged via line 29, can be used as a source of fuel for the reboiler-furnace in the enzyme makeup section and for steam/power generation. Overall cellulase enzyme recovery in adsorption stage 15 and wash train 25 amounts to at least 75%, and as much as about 85%, of the total supplied to the hydrolysis section.

Makeup enzyme is produced in fermentors 30 and 31 utilizing that portion of the output sugar solution removed by means of line 23, as noted above. The concentration of sugar in the product solution is generally above about 5% by weight which has been found to be too high a concentration to effectively support growth of the cellulolytic microorganism. It is, therefore, preferred to dilute the solution to approximately 0.5 – 3% by weight. The water necessary for dilution, together with a suitable nutrient composition, is introduced via line 32 and mixed with incoming sugar solution from line 23. Nutrient compositions suitable for submerged culture growth of a cellulase-producing fungal microorganism such as *Trichoderma viride* are reported by Mandels and Reese, *J. Bacteriol.*, 72, 269 (1957); *J. Bacteriol.*, 79, 816 (1960); and *J. Bacteriol.*, 83, 400 (1962). Another suitable nutrient material comprising a mixture of the inorganic chemicals $(NH_4)_2SO_4$, $KH_2PO_4$, $(NH_2)_2CO_2$, $CaCl_2$ and $MgSO_4 \cdot 7H_2O$ and proteose peptone is described by Mandels and Weber, *Adv. in Chem. Ser.*, 95, 391 (1969). It has been found that a mixture of cottonseed oil as a protein source and a superphosphate-containing fertilizer of the type readily available on the commercial market is equally suitable and much more economical. The nutrient material is added preferably in a concentration of substantially 5 – 12 mg/ml of appropriately diluted sugar solution. The growth medium is introduced into sterilizer 33 where it is heated to a suitably high temperature, for example, by heat exchange with condensing steam. Heating to a temperature of about 145°C will effectively sterilize the growth medium. The sterile medium is then fed to heat exchanger 26 via line 34 where it is cooled to a temperature suitable for fermentation. Cooling is preferably effected by heat exchange with wash water entering wash train 25, thereby heating the wash water to hydrolysis reaction temperature. The fermentation reaction is carried out at a temperature of from substantially 20°C to substantially 50°C, preferably around 30°C. The cooled, sterile medium, to which an inoculum of the desired microorganism is added in order to initiate growth, is fed into mycelium growth fermentor 30 for a period of time sufficient to exhaust essentially all of the sugars for growth of the cellulase-secreting microorganism. Mycelium from fermentor 30 is fed into enzyme growth fermentor 31 for production of enzyme in the presence of an appropriate inducer which is introduced by way of line 35. The presence of a cellulosic material is required to induce formation of the cellulase enzyme. The cellulosic material can be from any source, but for the present process, a portion of the feed from grinder 14 is most feasibly utilized as the inducer. Generally, an amount sufficient to provide a cellulose concentration of about 0.3 – 1.5% by weight in fermentor 31 is preferred. The plant feed is sterilized prior to introduction to the fermentor. Following enzyme production, mycelium solids are separated from the enzyme-containing liquid phase in filter 36.

The liquid stream containing the makeup enzyme is discharged from fermentor 31 by means of line 37. An organic solvent is added to the liquid stream by means of line 38 for enzyme precipitation. Although acetone is the preferred organic solvent, other lower alkyl (less than about 6 carbon atoms) ketones or alcohols, particularly methyl or ethyl alcohol, can also be used. The precipitated enzyme protein is separated in filter 39 and fed into hydrolyzer 19 by means of line 40. The liquid stream, discharged from filter 39 by means of line 41, is utilized for solvent recovery in distillation column 42. The distillation feed can be preheated by heat exchange with column bottoms in heat exchanger 43 and can be further heated in reboiler-furnace 44 before its entry to the distillation column. The reboiler-furnace can be fueled by combustion of spent solids from wash train 25 as noted above. Substantially all of the organic solvent is recovered from the top of the distillation column. Column bottoms are discharged via line 45 and can be cooled by preheating distillation feed in heat exchanger 43 and then recycled to the wash water stream for introduction to wash train 25. Makeup solvent is added by means of line 46 to the liquid stream from the distillation column top before being reused for solvent precipitation.

EXAMPLE

Considering now a specific example, waste paper containing substantially 6% moisture and having a cellulose content of substantially 61% is shredded and ground to −200 mesh size before being utilized for hydrolysis. Solid concentration in the hydrolysis vessel is 10%. The hydrolysis temperature is maintained at substantially 50°C and pH at substantially 4.8. For an enzyme activity of 2.7 Filter Paper, a residence time of 40 hours is maintained, corresponding to substantially 82% conversion.

Effluents from the hydrolyzer are passed through a filter to remove the unreacted solids from the enzyme and glucose solution. Approximately 51% of the hydrolyzer enzyme activity remains in the liquid phase after filtration, the rest being adsorbed on spent solids. To recover the adsorbed enzyme the filtered solids are washed in a series of countercurrent mixer-settlers and the wash water fed back to the hydrolysis vessel. The enzyme activity in the liquid phase is recovered by countercurrent adsorption on the incoming solid feed to the hydrolysis stage. The liquid stream from the adsorption step is the product output of reducing sugars as 5.58% solution.

A minor portion, substantially 7%, of the output sugar solution is diluted to an approximately 1% solution and mixed with a nutrient composition comprising cottonseed oil and a commercial fertilizer comprising superphosphate, the concentration of the nutrient material being substantially 10 mg/ml. The growth feed is sterilized at a temperature of substantially 144°C and cooled to a temperature of substantially 30°C. An inoculum of *Trichoderma viride* QM9414, described above, is added to the cooled, sterile feed just prior to introduction to a mycelium growth fermentor for growth of the fungus. Following growth of the fungus the culture is transferred to an enzyme growth fermentor to which an amount of sterilized plant feed sufficient to provide a cellulose concentration of substantially 1% is added as an enzyme inducer. Enzyme is produced at substantially 1.3 Filter Paper activity. After filtration to remove mycelium solids, the enzyme protein is precipitated from the culture broth by the addition thereto of acetone, the volume ratio of solvent to liquid being substantially 3:1. The precipitated enzyme is then fed to the hydrolysis vessel. Substantially all of the acetone is recovered from the filtrate by distillation. The spent solids from the hydrolyzer following washing are utilized as fuel for the reboiler-furnace for heating the feed to the distillation column and for steam/power generation.

Although the invention has been described specifically with respect to the enzymatic degradation of waste paper, it will be appreciated that the present invention is applicable to the treatment of cellulosic materials from other sources. Various modifications and changes in the process of the present invention will be obvious to those skilled in the art without departing from the true spirit and scope thereof, and thus it is not intended to limit the invention except by the terms of the following claims.

What we claim is:

1. A continuous process for enzymatically converting a cellulosic material to soluble sugar which comprises:
    a. hydrolyzing the cellulosic material by the degrading action of cellulase enzyme under conditions which promote conversion of cellulose to soluble sugar;

b. removing a stream of hydrolysis products from the hydrolysis stage, said hydrolysis products comprising a liquid sugar-containing phase and a solid phase containing unhydrolyzed spent solids, both of said phases containing cellulase enzyme from the hydrolysis stage;

c. adding a stream of fresh cellulosic material to the hydrolysis stage to replenish the cellulosic material converted to hydrolysis products;

d. contacting the liquid sugar-containing phase from step (b) with the added fresh cellulosic material prior to the introduction thereof to the hydrolysis stage, thereby recovering the cellulase enzyme contained in the liquid sugar-containing phase by adsorption on fresh cellulosic material;

e. recovering a stream of product sugar solution from step (d);

f. washing the solid phase containing unhydrolyzed spent solids from step (b) with a stream of water, thereby recovering cellulase adsorbed on said solids by solution in water;

g. adding the water containing recovered cellulase enzyme from step (f) to the hydrolysis stage; and h. providing a stream of makeup cellulase enzyme for the hydrolysis stage by the steps including:
  1. in a first zone, growing a cellulase-synthesizing microorganism on a minor portion of the product sugar solution, and
  2. in a second zone, contacting the microorganism-containing medium with an amount of cellulosic material sufficient to induce formation of cellulase enzyme under conditions substantially non-supportive of growth of the cellulase-secreting microorganism.

2. A process according to claim 1 wherein the cellulosic material is waste cellulosic material.

3. A process according to claim 1 further defined by utilizing in the hydrolysis reaction cellulase enzyme in an amount sufficient to provide an enzyme activity in the range from substantially 0.5 to substantially 6 Filter Paper activity.

4. A process according to claim 1 further defined by maintaining the temperature of the hydrolysis reaction in the range from substantially 30°C to substantially 60°C.

5. A process according to claim 1 further defined by maintaining the temperature during microorganism growth and during cellulase enzyme formation in the range from substantially 20°C to substantially 50°C.

6. A process according to claim 1 further defined by growing the cellulase-synthesizing microorganism in the presence of a nutrient composition comprising superphosphate and cottonseed oil.

7. A process according to claim 1 further defined by recovering the makeup cellulase enzyme from the culture medium by adding to the liquid phase thereof an organic solvent to precipitate the cellulose enzyme therefrom.

8. A process according to claim 7 wherein the organic solvent is acetone.

9. A process according to claim 7 further defined by recovering organic solvent from the liquid phase by distillation and utilizing spent unhydrolyzed solids as fuel to supply process heat for the distillation step.

* * * * *